United States Patent [19]

Hunt

[11] 4,166,904

[45] Sep. 4, 1979

[54] β-LACTAM CONTAINING COMPOUNDS

[75] Inventor: Eric Hunt, Reigate, England

[73] Assignee: Beecham Group Limited, Great Britain

[21] Appl. No.: 880,948

[22] Filed: Feb. 24, 1978

[30] Foreign Application Priority Data

Feb. 26, 1977 [GB] United Kingdom ............... 8240/77

[51] Int. Cl.² ............................................. C07D 263/52
[52] U.S. Cl. ................................... 542/427; 424/270;
424/271; 424/272; 424/114; 542/420; 544/30;
548/217
[58] Field of Search ................... 542/420, 427; 544/30;
424/270, 271, 272; 260/302 F, 307 FA

[56] References Cited

U.S. PATENT DOCUMENTS

| 3,925,363 | 12/1975 | Cama ..................... 260/307 FA X |
| 3,950,352 | 4/1976 | Wolfe ..................... 424/272 |
| 4,008,231 | 2/1977 | Wright ..................... 544/30 |

FOREIGN PATENT DOCUMENTS 840253 9/1976 Belgium .
2337447 2/1975 Fed. Rep. of Germany ............ 544/30
2337472 2/1975 Fed. Rep. of Germany ............ 544/30

OTHER PUBLICATIONS

Chem. Abs., Brown et al., "Naturally Occurring β Lactamase Inhibitors with Antibacterial Activity" vol. 85, 1976 92145g.

*Primary Examiner*—Arthur P. Demers
*Attorney, Agent, or Firm*—Jacobs & Jacobs

[57] ABSTRACT

Compounds of the formula (II)

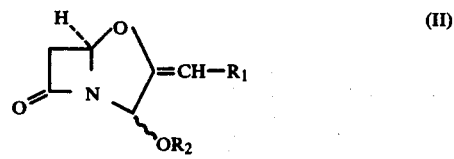

wherein
$R_1$ is $CH_3$, $CH_2OH$, $CHO$ or $CH_2OCOR_4$ wherein $R_4$ is a hydrocarbon of 1–7 carbon atoms and
$R_2$ is a group of the formula $R_3$ or $COR_3$ wherein $R_3$ is a hydrocarbon of 1–7 carbon atoms optionally inertly substituted by halogen are useful as antibacterial agents and β-lactamase inhibitory agents.

14 Claims, No Drawings

β-LACTAM CONTAINING COMPOUNDS

The present invention relates to antibacterial agents, to their preparation and to compositions containing them.

Belgian Pat. No. 827,926 discloses inter alia that clavulanic acid, which has the formula (I):

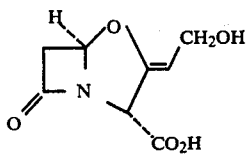
(I)

and its salts and ester are β-lactamase inhibitors useful for enhancing the effectiveness of penicillins and cephalosporins. Isoclavulanic acid is described in Belgian Pat. No. 836,652 and U.S. Ser. No. 638,373 and deoxyclavulanic acid is described in Belgian Pat. No. 840,253 and U.S. Ser. No. 669,697. The surprising discovery has now been made that the 3-carboxyl group need not be present for the compound to possess β-lactamase inhibitory activity.

The present invention provides the compounds of the formula (II):

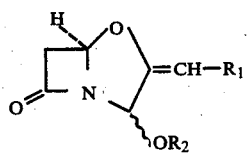
(II)

wherein $R_1$ is a $CH_3$, $CH_2OH$, $CHO$ or a group $CH_2O\text{-}COR_4$ where $R_4$ is a hydrocarbon group of 1–7 carbon atoms and $R_2$ is a group of the formula $R_3$ or $COR_3$ where $R_3$ is a hydrocarbon group of 1–7 carbon atoms optionally inertly substituted by halogen.

One group of particularly suitable compounds of the formula (II) are those of the formula (III):

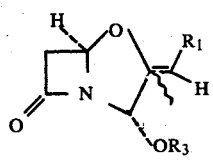
(III)

wherein $R_3$ is as defined in relation to formula (II).

A further group of particularly suitable compounds of the formula (II) are those of the formula (IV):

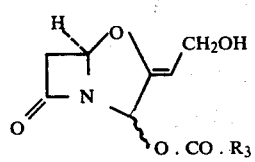
(IV)

wherein $R_3$ is as defined in relation to formula (II).

Suitable groups $R_3$ for inclusion in the compounds of the formulae (III) and (IV) include alkyl groups such as the methyl, ethyl and propyl groups and aryl or aralkyl groups such as the phenyl, chlorophenyl, benzyl, chlorobenzyl or like group.

Particularly suitable groups $R_3$ for inclusion in the compounds of the formula (III) include alkyl groups. Particularly suitable groups $R_3$ for inclusion in the compounds of the formula (IV) include optionally substituted phenyl groups.

The present invention also provides a pharmaceutical composition which comprises a compound of the formula (II) and a pharmaceutically acceptable carrier therefore.

Most suitably the composition of this invention also contains a penicillin or cephalosporin.

Suitable forms of the compositions of this invention are those described in Belgian Pat. No. 827,926 as being suitable for compositions containing clavulanic acid.

The present invention also provides a process for the preparation of the compounds of the formula (II) wherein $R_2$ is a group $R_3$ wherein $R_3$ is as defined in relation to formula (II) which process comprises the oxidative decarboxylation of a compound of the formula (V):

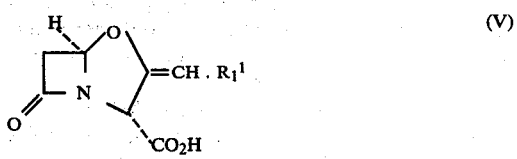
(V)

or a salt thereof wherein $R_1{}^1$ is a $CH_2OH$ or $CH_3$ group in a water-free medium containing a compound of the formula $R_3OH$ said oxidation being effected by the passage of a current between platinum electrodes; and thereafter if desired oxidizing the allylic alcohol to an allylic aldehyde or acylating the allylic alcohol.

Normally this reaction is performed in an organic solvent when it consists of or comprises as a major proportion, the compound of the formula $R_3OH$.

Most suitably the reaction is effected at a depressed non-extreme temperature such as $-50°$ to $-10°$ C. and more usually at about $-40°$ to $-30°$ C.

Normally a current density of 50–2000 mA/sq. cm, usually 100–500 mA/sq.cm, for example 120–300 mA/sq.cm is employed between platinum foil electrodes placed 1 to 4 mm apart.

Once the reaction is substantially complete the product may be isolated in conventional manner, for example removal of the solvent under reduced pressure and chromatographic purification of the resulting material.

A second method for conducting the oxidative decarboxylation process of this invention comprises heating a compound of formula (V) with a compound of formula $(V^1)$:

$$Pb(OCOR_3)_4 \qquad (V^1)$$

wherein $R_3$ is defined in relation to formula (II), in an inert organic solvent.

Suitable organic solvents include tetrahydrofuran, 1,2-dimethoxyethane, benzene, toluene, xylene, and the like, and mixtures of these solvents. A particularly suitable solvent consists of a mixture of 1,2-dimethoxyethane and benzene. The solvent must be water-free and the reaction is conducted in an inert atmosphere such as nitrogen or argon.

The reaction is best conducted at an elevated temperature, such as 40° to 120° C, more suitably at 50° to 80° C.

Oxidation of the allylic hydroxyl group may be effected using the method disclosed in Belgian Pat. No. 846,678 and U.S. Ser. No. 717,900 acylation of the allylic hydroxyl group may be effected using the method disclosed in Belgian Pat. No. 834,645 and U.S. Ser. No. 620,564.

The present invention also provides a process for the preparation of a compound of the formula (II) wherein $R_2$ is a group of the formula $OR_3$ wherein $R_3$ is as defined in relation to formula (II) which process comprises the elimination of the elements of $CO_2$ from a compound of the formula (VI):

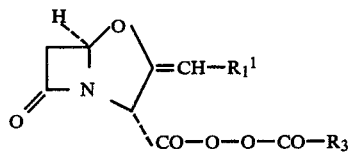

wherein $R_1{}^1$ is a $CH_2OH$ or $CH_3$ group and $R_3$ is as defined in relation to formula (II) and thereafter if desired oxidizing the allylic alcohol to an aldehyde or acylating the allylic alcohol.

The compounds of the formula (VI) tend to undergo decarboxylation, spontaneously. The decarboxylation is thought to proceed via rearrangement to compounds of formula (VII):

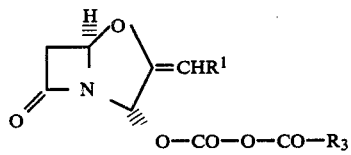

The rearrangement and decarboxylation can be encouraged by allowing a cold solution of the compound of the formula (VI) in an inert organic solvent to warm, for example by allowing or causing a solution of the compound of the formula (VI) in dimethoxyethane, methylene chloride and/or ethyl acetate at a temperature less than 5° C. to warm to a temperature such as 20°-30° C.

The compounds of the formula (VI) may be isolated in conventional manner for example by evaporation of the solvent followed by chromatography.

The compounds of the formula (VI) may be prepared by the reaction of a corresponding compound of the formula (V):

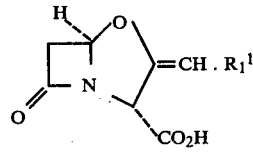

and a per acid of the formula $HO.O.CO.R_3$ in the presence of dicyclohexylcarbodiimide.

This reaction is normally carried out in an inert organic solvent such as those described above at a depressed temperature.

A compound of formula (II) wherein $R_1$ is a $CH_2OH$ or acylated $CH_2OH$ group may be converted into a compound of formula (II) wherein $R_1$ is a $CH_3$ group by hydrogenolysis over a palladium catalyst in a solvent such as tetrahydrofuran.

EXAMPLE 1

(Z)-(5R)-3-(2-Hydroxyethylidene)-2-methoxy-4-oxa-1-azabicyclo[3.2.0]heptan-7-one

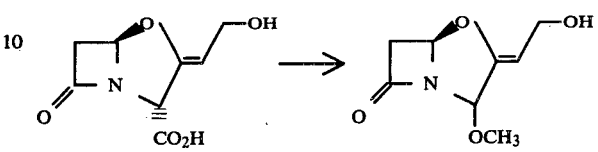

Sodium clavulanate tetrahydrate (1.5 g.) was dissolved in a mixture of saturated brine (15 ml.) and ethyl acetate (15 ml.). The solution was stirred and ice-cooled while 1 N hydrochloric acid (5 ml.) was added dropwise over 2 minutes. The mixture was then shaken and the layers were separated. The aqueous layer was extracted twice with ethyl acetate (15 ml. portions) and the combined organic layers were washed once with saturated brine (10 ml.). The ethyl acetate solution was dried (sodium sulphate) and the solvent was removed by evaporation under reduced pressure to yield clavulanic acid (containing ca 0.5 meq. ethyl acetate) as a colourless gum (930 mg.)

The gum was dissolved in anhydrous methanol (15 ml.) containing triethylamine (80 mg.). The solution was stirred at $-30°$ to $-40°$ and was electrolysed using a pair of platinum-foil electrodes (1.8×0.9 cm.) placed 1 mm apart passing a current of 200–250 mA for 40 minutes. The mixture was filtered and the filtrate was diluted with benzene (50 ml.). The solution was concentrated to ca 10 ml. by evaporation of solvent under reduced pressure and the concentrated solution was diluted with ethyl acetate (50 ml.). The solution was washed with saturated brine (10 ml.) and was dried (magnesium sulphate). Evaporation of solvent under reduced pressure yielded a yellow gum (350 mg.) which was chromatographed on silica gel (10 g.) using ethyl acetate/petroleum ether (b.p. 60°–80°) to give the title compound as a colourless gum (15 mg.) $[\alpha]_D^{22} = +45.5°$ (c=0.75, $CHCl_3$). (Found: $M^+$, 185.0672. $C_8H_{11}NO_4$ requires 185.0688). $\nu_{max}$ ($CHCl_3$): 3550, 3370 (hydroxyl OH), 1800 (β-lactam C=O), 1698 (olefinic C=C)cm$^{-1}$. δ ($CDCl_3$): 1.55 (br.s, 1H, OH), 2.96 (d, J 16 Hz, 1H C(6)H), 3.35 (dd, J 16, J' 2 Hz, 1H, C(6)H), 3.38 (s, 3H, $OCH_3$), 4.20 (d, J 6 Hz, 2H, $CH_2O$), 4.89 (t, J 6 Hz, 1H olefinic H), 5.27 (s, 1H, C(2)H), 5.53 (d, J 2 Hz, 1H, C(5)H). m/e: 185 ($M^+$, 6%), 168(2), 153(7), 102(17), 87(53), 86(25), 85(18), 72(100), 69(72)

EXAMPLE 2

(Z)-(5R)-2-Methoxy-3-(2-phenylacetoxyethylidene)-4-oxa-1-azabicyclo[3.2.0]heptan-7-one

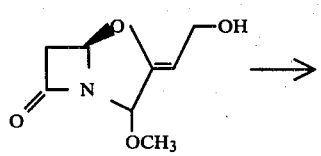

-continued

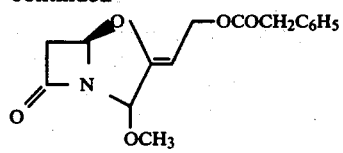

(Z)-(5R)-3-(2-Hydroxyethylidene)-2-methoxy-4-oxa-1-azabicyclo[3.2.0]heptan-7-one (15 mg.) was dissolved in dry diethyl ether (2 ml.) and the solution was stirred and ice-cooled with exclusion of moisture while phenylacetyl chloride (30 mg.) followed by dry pyridine (15 mg.) were added. The mixture was kept at 4° with exclusion of moisture for 15 hours. The mixture was diluted with ethyl acetate (30 ml.) and was washed with 5% sodium chloride solution (10 ml.) and saturated sodium chloride solution (10 ml.). The solution was dried (magnesium sulphate) and the solvent was evaporated under reduced pressure to yield a yellow gum. Chromatography of the gum on silica gel (10 g.) using ethyl acetate/petroleum ether (b.p. 60°-80°) gave the title compound as a colourless gum (17 mg.). $[\alpha]_D^{22} = +45.6°$ (c=1.0, CHCl$_3$). $\nu_{max}$ (CHCl$_3$): 1798 ($\beta$-lactam C=O), 1730 (ester C=O), 1710 (sh.) (olefinic C=C)cm$^{-1}$. $\delta$ (CDCl$_3$): 2.96 (d, J 16 Hz, 1H, C(6)H), 3.34 (dd, J 16, J' 2 Hz, 1H, C(6)H), 3.36 (s, 3H, OCH$_3$), 3.56 (s, 2H, CH$_2$Ar), 4.60–4.90 (complex, 3H, CH$_2$O and olefinic H), 5.25 (s, 1H, C(2)H), 5.52 (d, J 2 Hz, 1H, C(5)H), 7.22 (s, 5H, Ar-H). m/e: 234 (2%), 229 (C$_{13}$H$_{11}$NO$_3$, 13%), 168 (19), 118 (12), 99 (22), 91 (100).

EXAMPLE 3 (a)

(Z)-(2S, 5R)-2-(m-Chlorobenzoyloxy)-3-(2-hydroxyethylidene)-4-oxa-1-azabicyclo[3.2.0]heptan-7-one

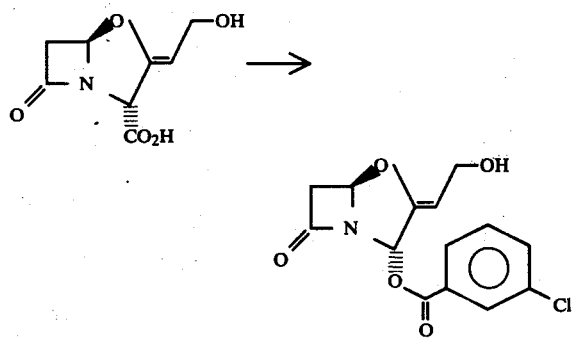

Clavulanic acid (containing ca 0.5 meq. ethyl acetate; 410 mg., 1.7 mmole) was dissolved in dry 1,2-dimethoxyethane/methylene chloride (1:1, 10 ml.). The solution was stirred and ice-cooled with exclusion of moisture while m-chloroperbenzoic acid (380 mg.) and dicyclohexylcarbodiimide (400 mg.) were added. The mixture was stirred with exclusion of moisture for 3 hours at 0° and then for 15 hours at room temperature. The mixture was diluted with ethyl acetate (50 ml.) and was filtered. The filtrate was washed with saturated sodium bicarbonate solution and then with saturated brine. The solution was dried (magnesium sulphate and the solvent was evaporated under reduced pressure to yield a yellow gum. The gum was chromatographed on silica gel (25 g.) using ethyl acetate/petroleum ether (b.p. 60°-80°) to give the title compound as a colourless gum (60 mg., 11% yield). $[\alpha]_D^{21} + 88.8°$ (c=1.0 CHCl$_3$). $\nu_{max}$ (CHCl$_3$): 3320 (hydroxyl OH), 1805 ($\beta$-lactam C=O), 1730 (ester C=O), 1700 (olefinic C=C)cm$^{-1}$. $\delta$ (CDCl$_3$): 2.28 (br.s, 1H, OH), 3.11 (d, J 16 Hz, 1H, C(6)H), 3.48 (dd, J 16, J' 2 Hz, 1H, C(6)H), 4.26 (d, J 7 Hz, 2H, CH$_2$O), 5.03 (t, J 7 Hz, 1H, olefinic H), 5.77 (d, J 2 Hz, 1H, C(5)H), 6.70 (s, 1H, C(2)H), 7.25–7.60 (m, 2H, Ar-H), 7.80–8.00 (m, 2H, Ar-H).

EXAMPLE 3 (b)

Clavulanic acid (440 mg., 1.8 mmole) was dissolved in dry 1,2-dimethoxyethane (10 ml.) and the solution was stirred with exclusion of moisture at −30° while N-methylmorpholine (180 mg., 1.8 mmole) followed by ethyl chloroformate (195 mg., 1.8 mmole) were added. After addition, the mixture was stirred at −30° for 15 minutes, and was then cooled to −70° and m-chloroperbenzoic acid (310 mg., 1.8 mmole) in dry methylene chloride (3 ml.) was added dropwise. The mixture was stirred at −70° for 2 hours and then the cooling bath was removed and stirring was continued for 17 hours. The mixture was diluted with ethyl acetate (50 ml) and was filtered. The filtrate was washed with 5% citric acid solution, saturated sodium bicarbonate solution, and saturated brine. The solution was dried (magnesium sulphate) and the solvent was evaporated under reduced pressure to yield a colourless gum. Chromatography of the gum on silica gel (20 g.) using ethyl acetate/petroleum ether (b.p. 60°-80°) gave as a colourless gum (68 mg.) the title compound as described in Example 3 (a).

EXAMPLE 4

(Z)-(2S, 5R)-2-(m-Chlorobenzoyloxy)-3-(2-phenylacetoxyethylidene)-4-oxa-1-azabicyclo[3.2.0]heptan-7-one

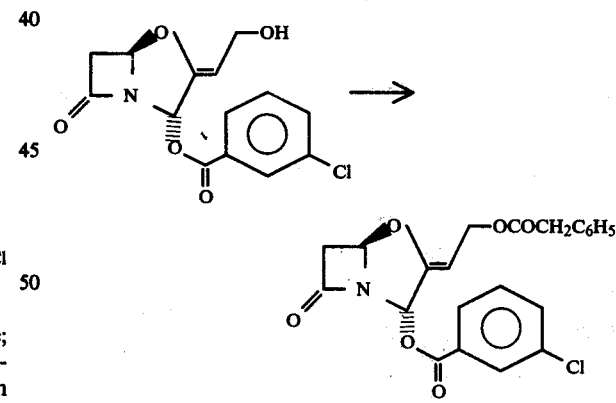

(Z)-(2S, 5R)-2-(m-Chlorobenzoyloxy)-3-(2-hydroxyethylidene)-4-oxa-1-azabicyclo[3.2.0]heptan-7-one (80 mg., 0.26 mmole) was converted into the title compound using the process described in Example 2. The title compound was obtained as a colourless gum (100 mg., 91% yield). $[\alpha]_D^{23} = +59.4°$ (c=1.0, CHCl$_3$). $\nu_{max}$ (CHCl$_3$): 1805 ($\beta$-lactam C=O), 1730 (ester C=O), 1700 (sh., olefinic C=C)cm$^{-1}$. $\delta$ (CDCl$_3$): 3.03 (d, J 16 Hz, 1H, C(6)H), 3.40 (dd, J 16, J' 2 Hz, 1H, C(6)H), 3.53 (s, 2H, ArCH$_2$), 4.60–5.00 (complex, 3H, CH$_2$O and olefinic H), 5.70 (d, J 2 Hz, 1H, C(5)H), 6.63 (s, 1H, C(2)H), 7.10–7.95 (complex, 9H, Ar-H).

EXAMPLE 5

(Z)-(5R)-2-Acetoxy-3-(2-hydroxyethylidene)-4-oxa-1-azabicyclo[3.2.0]heptan-7-one,
(Z)-(5R)-2-acetoxy-3-(2-acetoxyethylidene)-4-oxa-1-azabicyclo[3.2.0]heptan-7-one, and
(5R)-2-acetoxy-3-formylmethylene-4-oxa-1-azabicyclo[3.2.0]heptan-7-one

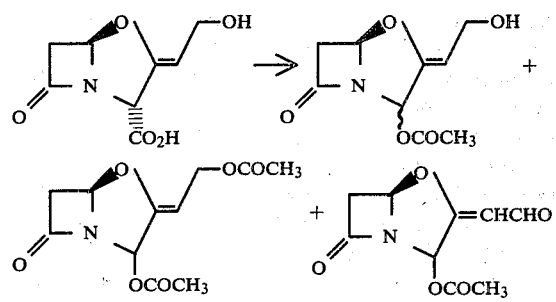

Clavulanic acid (containing ca 0.5 meq. ethyl acetate; 2.0 g., 8.1 mmole) was dissolved in dry 1,2-dimethoxyethane (10 ml)/dry benzene (20 ml.). The solution was stirred under a dry nitrogen atmosphere while dry lead tetraacetate (3.7 g., 8.4 mmole) was added in one portion. The mixture was then stirred under a dry nitrogen atmosphere and heated at 70° (bath temperature) for 20 minutes. The mixture was cooled, diluted with ethyl acetate (100 ml.), and filtered. The filtrate was washed with saturated sodium bicarbonate solution (30 ml.) and saturated brine (30 ml.). The solution was dried (magnesium sulphate) and the solvent was evaporated under reduced pressure to yield a yellow gum (380 mg.). The gum was chromatographed on silica gel (25 g.) using ethyl acetate/petroleum ether (b.p. 60°-80°) to give, in order of elution, the following compounds. (Z)-(5R)-2-Acetoxy-3-(2-acetoxyethylidene)-4-oxa-1-azabicyclo[3.2.0]heptan-7-one as a colourless gum (32 mg.). $[\alpha]_D^{22} = +102.1°$ (c=1.0, CHCl$_3$). $\nu_{max}$ (CHCl$_3$): 1805 ($\beta$-lactam C=O), 1740 (ester C=O), 1700 (sh., olefinic C=C)cm$^{-1}$. $\delta$ (CDCl$_3$): 2.01 (s, 3H, OCOCH$_3$), 2.04 (s, 3H, OCOCH$_3$), 3.04 (d, J 16 Hz, 1H, C(6)H), 3.42 (dd, J 16, J' 2 Hz, 1H, C(6)H), 4.50-4.95 (complex, 3H, CH$_2$O and olefinic H), 5.65 (d, J 2 Hz, 1H, C(5)H), 6.45 (s, 1H, C(2)H).

(5R)-2-Acetoxy-3-formylmethylene-4-oxa-1-azabicyclo[3.2.0]heptan-7-one as a colourless oil (33 mg.). $[\alpha]_D^{22} = +95.6°$ (c=1.0, CHCl$_3$). $\lambda_{max}$ (EtOH): 254 nm ($\epsilon$ 14,300). $\nu_{max}$ (CHCl$_3$): 2800 (formyl CH), 1807 ($\beta$-lactam C=O), 1750 (ester C=O), 1675 (aldehyde C=O), 1663 (olefinic C=C)cm$^{-1}$. $\delta$ (CDCl$_3$): 2.05 (s, 3H, OCOCH$_3$), 2.90-3.65 (complex, 2H, C(6)H$_2$), 5.32 (d, J 7 Hz, 1H, olefinic H), 5.90 (d, J 2 Hz, 1H, C(5)H), 6.44 (s, 1H, C(2)H), 9.53 (d, J 7 Hz, 0.3H, CHO), 9.85 (d, J 7 Hz, 0.7H, CHO).

(Z)-(5R)-2-Acetoxy-3-(2-hydroxyethylidene)-4-oxa-1-azabicyclo[3.2.0]heptan-7-one as a colourless gum (145 mg.). $[\alpha]_D^{22} = +145.8°$ (c=0.64, CHCl$_3$). $\nu_{max}$ (CHCl$_3$): 3500 and 3320 (hydroxyl OH), 1803 ($\beta$-lactam C=O), 1750 (ester C=O), 1698 (olefinic C=C)cm$^{-1}$. $\delta$ (CDCl$_3$): 1.90 (s, 1H, OH), 2.03 (s, 3H, OCOCH$_3$), 3.00 (d, J 16 Hz, 1H, C(6)H), 3.41 (dd, J 16, J' 2 Hz, 1H, C(6)H), 4.18 (d, J 7 Hz, 2H, CH$_2$O), 4.90 (t, J 7 Hz, 1H, olefinic H), 5.63 (d, J 2 Hz, C(5)H), 6.42 (s, 1H, C(2)H).

EXAMPLE 6

(Z)-(5R)-2-Acetoxy-3-ethylidene-4-oxa-1-azabicyclo[3.2.0]-heptan-7-one and
(E)-(5R)-2-Acetoxy-3-(2-hydroxyethylidene)-4-oxa-1-azabicyclo[3.2.0]heptan-7-one

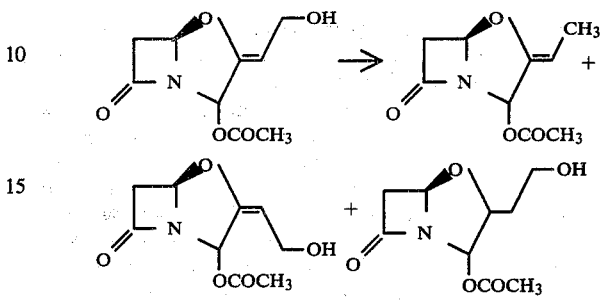

(Z)-(5R)-2-Acetoxy-3-(2-hydroxyethylidene)-4-oxa-1-azabicyclo[3.2.0]heptan-7-one (130 mg.) was dissolved in tetrahydrofuran (10 ml) and the solution was shaken with 10% palladium-on-charcoal (60 mg.) under one atmosphere of hydrogen at room temperature for 2 hours. The catalyst was removed by filtration and was washed with ethyl acetate. The solvent was evaporated under reduced pressure from the combined filtrate and washings to yield a colourless gum. The gum was chromatographed on silica gel (15 g.) using ethyl acetate/petroleum ether (b.p. 60°-80°) to give, in order of elution, the following compounds. (Z)-(5R)-2-Acetoxy-3-ethylidene-4-oxa-1-azabicyclo[3.2.0]-heptan-7-one as a colourless oil (6 mg., 5%). $\nu_{max}$ (CHCl$_3$): 1805 ($\beta$-lactam C=O), 1750 (ester C=O), 1703 (olefinic C=C)cm$^{-1}$. $\delta$ (CDCl$_3$): 1.62 (dd, J 6.5, J' 0.5 Hz, 3H, CH$_3$), 2.03 (s, 3H, OCOCH$_3$), 2.98 (d, J 16 Hz, 1H, C(6)H), 3.35 (dd, J 16, J' 2.5 Hz, 1H, C(6)H), 4.66 (q, J 6.5 Hz, 1H, olefinic H), 5.57 (d, J 2.5 Hz, 1H, C(5)H), 6.41 (br.s, 1H, C(2)H), (E)-(5R)-2-Acetoxy-3-(2-hydroxyethylidene)-4-oxa-1-azabicyclo[3.2.0]heptan-7-one as a colourless gum (14 mg., 11%). $\nu_{max}$ (CHCl$_3$): 3520, 3320 (alcohol OH), 1805 ($\beta$-lactam C=O), 1750 (ester C=O), 1695 (olefinic C=C)cm$^{-1}$. $\delta$ (CDCl$_3$): 1.67 (s, 1H, OH), 2.06 (s, 3H, OCOCH), 2.99 (d, J 16 Hz, 1H, C(6)H), 3.38 (dd, J 16, J' 2 Hz, 1H, C(6)H), 4.03 (d, J 8 Hz, 2H, CH$_2$O), 5.30 (dt, J 1, J' 8 Hz, 1H, olefinic H), 5.61 (d, J 2 Hz, 1H, C(5)H), 6.62 (d, J 1 Hz, 1H, C(2)H).

(Z)-(5R)-2-Acetoxy-3-(2-hydroxyethylidene)-4-oxa-1-azabicyclo[3.2.0]heptan-7-one (68 mg., 52%) and (5R)-2-acetoxy-3-(2-hydroxyethyl)-4-oxa-1-azabicyclo[3.2.0]heptan-7-one as a colourless gum (20 mg., 15%).

EXAMPLE 7

$\beta$-Lactamase inhibitory activity and antibacterial synergy

I$_{50}$ values were determined for the compound from Example 2 using the process described in Belgium Pat. No. 827,926. The results are given below.

| Source of $\beta$-lactamase | Staph. aureus Russell | Pseudomonas aeruginosa Dalgleish | E. coli JT 4 | Proteus mirabilis C889 |
|---|---|---|---|---|
| I$_{50}$ ($\mu$g/ml) | 0.48 | 0.24 | 0.48 | 3.4 |

The compound from Example 2 in combination with ampicillin showed synergy against *Staphylococcus aureus* Russell as indicated below.

| Concentration of inhibitor (μg/ml) | M.I.C. (μg/ml) for ampicillin | M.I.C. (μg/ml) for inhibitor |
|---|---|---|
| — | — | 62 |
| None | 250 | — |
| 1 | 2.5 | — |
| 5 | 0.6 | — |
| 20 | 0.08 | — |

I claim:

1. A compound of the formula (II)

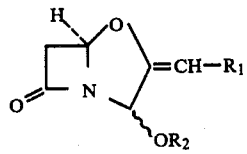

(II)

wherein $R_1$ is $CH_3$, $CH_2OH$, CHO or $CH_2OCOR_4$ wherein $R_4$ is a hydrocarbon of 1–7 carbon atoms and $R_2$ is a group of the formula $R_3$ or $COR_3$ wherein $R_3$ is a hydrocarbon of 1–7 carbon atoms unsubstituted or substituted by halogen.

2. A compound according to claim 1 of the formula (III)

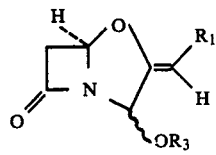

(III)

wherein $R_1$ is $CH_3$, $CH_2OH$, CHO or $CH_2OCOR_4$ wherein $R_4$ is a hydrocarbon of 1–7 carbon atoms and $R_3$ is alkyl of 1–7 carbon atoms, aryl unsubstituted or substituted by halogen or aralkyl unsubstituted or substituted in the aromatic ring by halogen.

3. A compound according to claim 2 wherein $R_3$ is methyl, ethyl, propyl, phenyl, chlorophenyl, benzyl or chlorobenzyl.

4. A compound according to claim 1 of the formula (IV)

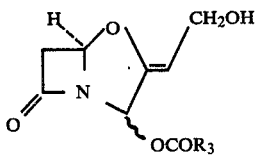

(IV)

wherein $R_3$ is alkyl of 1–7 carbon atoms, aryl unsubstituted or substituted by halogen or aralkyl unsubstituted or substituted in the aromatic ring by halogen.

5. A compound according to claim 4 wherein $R_3$ is phenyl, chlorophenyl, benzyl or chlorobenzyl.

6. (Z)-(5R)-3-(2-Hydroxyethylidene)-2-methoxy-4-oxa-1-azabicyclo[3.2.0]heptan-7-one.

7. (Z)-(5R)-2-Methoxy-(3-phenylacetoxyethylidene)-4-oxa-1-azabicyclo[3.2.0]heptan-7-one.

8. (Z)-(2S, 5R)-2-(m-Chlorobenzoyloxy)-3-(2-hydroxyethylidene)-4-oxa-1-azabicyclo[3.2.0]heptan-7-one.

9. (Z)-(2S,5R)-2-(m-Chlorobenzoyloxy)-3-(2-phenylacetoxyethylidene)-4-oxa-1-azabicyclo[3.2.0]heptan-7-one.

10. (Z)-(5R)-2-Acetoxy-3-(2-hydroxyethylidene)-4-oxa-1-azabicyclo[3.2.0]heptan-7-one.

11. (Z)-(5R)-2-Acetoxy-3-(2-acetoxyethylidene)-4-oxa-1-azabicyclo[3.2.0]heptan-7-one.

12. (5R)-2-Acetoxy-3-formylmethylene-4-oxa-1-azabicyclo[3.2.0]heptan-7-one.

13. (Z)-(5R)-2-Acetoxy-3-ethylidene-4-oxa-1-azabicyclo[3.2.0]heptan-7-one.

14. (E)-(5R)-2-Acetoxy-3-(2-hydroxyethylidene)-4-oxa-1-azabicyclo[3.2.0]heptan-7-one.

* * * * *